US012685668B2

(12) United States Patent
Chauhan et al.

(10) Patent No.: US 12,685,668 B2
(45) Date of Patent: Jul. 21, 2026

(54) DEVICES AND METHODS FOR AUTOMATED DELIVERY OF OPHTHALMOLOGICAL MEDICATIONS

(71) Applicant: University of Florida Research Foundation, Inc., Gainesville, FL (US)

(72) Inventors: Anuj Chauhan, Gainesville, FL (US); Brett Banther, Gainesville, FL (US); Shawn Lyvers, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 955 days.

(21) Appl. No.: 17/784,313

(22) PCT Filed: Dec. 11, 2020

(86) PCT No.: PCT/US2020/064581
§ 371 (c)(1),
(2) Date: Jun. 10, 2022

(87) PCT Pub. No.: WO2021/119473
PCT Pub. Date: Jun. 17, 2021

(65) Prior Publication Data
US 2023/0051700 A1     Feb. 16, 2023

Related U.S. Application Data

(60) Provisional application No. 62/947,280, filed on Dec. 12, 2019.

(51) Int. Cl.
*A61F 9/00* (2006.01)
*B65D 47/18* (2006.01)
*G02B 27/01* (2006.01)

(52) U.S. Cl.
CPC ............ *A61F 9/0026* (2013.01); *B65D 47/18* (2013.01); *G02B 27/017* (2013.01); *A61F 2250/0008* (2013.01)

(58) Field of Classification Search
CPC .................. A61F 9/0008; A61F 9/0026; A61F 2009/0035; A61M 35/00; A61M 35/20
See application file for complete search history.

(56) References Cited

U.S. PATENT DOCUMENTS 2,268,202 A     12/1941   Britton
2,513,701 A     7/1950    Woodford
(Continued)

FOREIGN PATENT DOCUMENTS

CN          109620532 A  *  4/2019   ........... A61F 9/0026

OTHER PUBLICATIONS

International search report for PCT/US20/64581 mailed Apr. 22, 2021.

*Primary Examiner* — Catharine L Anderson
(74) *Attorney, Agent, or Firm* — Thomas | Horstemeyer, LLP

(57) ABSTRACT

Disclosed are various embodiments for an apparatus for installation of eye drops, an automatic dispensing device, and a method to dispense eye drops. The apparatus including a dispensing device, a control system, and a housing. The dispensing device configured to dispense a dosage of a fluid medication from an eye drop bottle, the eye drop bottle having an opening. The control system operatively connected to the dispensing device. The housing comprising a main wearable headset and a cover. The housing configured to contain the dispensing device and the control system, and configured to allow passage of the dosage of the fluid medication through an aperture in the main wearable headset of the housing. Also, disclosed is an automatic dispensing device comprising a motor and detection system to dispense a fluid from a bottle.

20 Claims, 11 Drawing Sheets

(56)  References Cited

U.S. PATENT DOCUMENTS

| | | | | |
|---|---|---|---|---|
| 3,248,011 | A | 4/1966 | Benjamin | |
| 7,201,732 | B2 | 4/2007 | Anderson et al. | |
| 8,128,606 | B2 | 3/2012 | Anderson et al. | |
| 8,734,408 | B2 | 5/2014 | Marx | |
| 9,039,666 | B2 * | 5/2015 | Voss | A61F 9/0026 |
| | | | | 604/290 |
| 9,610,192 | B2 | 4/2017 | Marx | |
| 10,314,740 | B2 * | 6/2019 | Kraft | G07F 17/0092 |
| 12,186,234 | B2 * | 1/2025 | Ivri | A61F 9/0008 |
| 2005/0240162 | A1 * | 10/2005 | Chen | A61F 9/0008 |
| | | | | 604/298 |
| 2006/0253086 | A1 | 11/2006 | Moberg et al. | |
| 2014/0213989 | A1 * | 7/2014 | Kelly | A61F 9/0008 |
| | | | | 604/296 |
| 2017/0028130 | A1 | 2/2017 | Perazzo et al. | |
| 2017/0196732 | A1 * | 7/2017 | Marx | A61F 9/0026 |
| 2018/0193190 | A1 * | 7/2018 | Ajaelo | G16H 20/13 |

* cited by examiner

FIG. 9A          FIG. 9B

DEVICES AND METHODS FOR AUTOMATED DELIVERY OF OPHTHALMOLOGICAL MEDICATIONS

CROSS REFERENCE TO RELATED APPLICATIONS

This application is the 35 U.S.C. § 371 national stage application of PCT Application No. PCT/US2020/064581, filed Dec. 11, 2020, which claims priority to, and the benefit of, U.S. provisional application entitled "DEVICES AND METHODS FOR AUTOMATED DELIVERY OF OPH-THALMOLOGICAL MEDICATIONS" having Ser. No. 62/947,280, filed Dec. 12, 2019, both of which are hereby incorporated by reference herein in their entireties.

BACKGROUND

Ophthalmological medications are frequently delivered directly to the eye in a fluid form, commonly known as eye drops. Such ophthalmological medications, can be pre-scribed by doctor for treatment of acute or chronic condi-tions, or may be available over the counter. Eye drops commonly contain saline and can have active ingredients, for example, steroids, antihistamines, antibiotics, antifungal, or topical anesthetics. However, eye drops can also be provided without medications as lubricating and tear-replac-ing solutions.

A common problem with the instillation of ophthalmo-logical fluids, or eye drops, is that the patient may blink during delivery causing inconsistent or ineffective dosages. Additionally, it can be difficult for a patient to deliver the eye drops with touching the delivery tip to the eye, which may cause irritation or injury to the patient and may contaminate the ophthalmological solution with bacteria, fungi, or viruses.

SUMMARY

Aspects of the present disclosure are related to delivery of ophthalmological medications. In one aspect, among others, a dispensing device comprises a motor connected to a lead screw, a movable mount, a yoke, a pair of pivot arms, and a bottle containing a fluid. The motor can be configured to rotate the lead screw in either a first rotational direction or a second rotational direction. The movable mount can com-prise a body, a pair of opposing mount pins, and a threaded hole that transverses the body in a direction orthogonal to the opposing mount pins, wherein the movable mount is threaded on the lead screw via the threaded hole. The moveable mount can be configured to translate on the lead screw in a first direction, when the lead screw is rotating in a first rotational direction, and a second direction, when the lead screw is rotating in a second direction. The yoke can comprise a shaft with a pair of opposing yoke pins and a pair of yoke arms extending orthogonally from the shaft, each yoke arm having a distal end with a yoke hole. The yoke can be configured to pivot about a fixed position via the pair of yoke holes. Each pivot arm can have a mount aperture and a pivot aperture, each mount aperture configured to receive the respective mount pin, each pivot aperture configured to receive the respective yoke pin, each pivot arm pivotably connected to the mount and the yoke. The bottle can have a deformable side and can have an opening. The bottle can be positioned at a distance from the shaft of the yoke such that in response to movement of the movable mount, the shaft of the yoke is configured to move in a curved path and press the deformable side of the bottle to dispense the fluid.

In various aspects, the dispensing device can comprise a pair of slotted plates, each slotted plate having a relief with a pin configured to receive the yoke via the respective yoke holes, each slotted plate having a curved slot configured to receive and guide the respective yoke pin, each slotted plate having a linear slot configured to receive and guide the respective mount pin. The curved slot can be connected to the linear slot. The dispensing device can comprise: a removable bottle magazine configured to receive the bottle containing the fluid; and a dispenser housing comprising a seat and a dispensing aperture, the seat configured to receive the bottle magazine. A slotted plate can be fixed to the dispenser housing or can be integrally formed in the dis-penser housing.

In some aspect, the dispensing device can comprise a local control processor, the local control processor config-ured to control the motor. The dispensing device can com-prise a lower limit switch. The lower limit switch can be configured to send a signal to turn off the motor, in response to the movable mount triggering the lower limit switch. The dispensing device can comprise an upper limit switch. The upper limit switch can be configured to send a signal reverse the rotational direction of the motor, in response to the movable mount triggering the upper limit switch. The dis-pensing device can comprise a drop sensing LED configured to send a signal reverse the rotational direction of the motor, in response to the drop sensing LED detecting that the dosage has been released.

In another aspect, an apparatus for installation of eye drops can comprise a dispensing device configured to dis-pense a dosage of a fluid medication from an eye drop bottle, the eye drop bottle having an opening; a control system operatively connected to the dispensing device; and a hous-ing. The housing can comprise a main wearable headset and a cover. The housing can be configured to contain the dispensing device and the control system. The housing can be configured to allow passage of the dosage of the fluid medication through an aperture in the main wearable headset of the housing. In one or more aspects, the apparatus can comprise a button interface panel operatively connected to the control system, the control system configured to operate the dispensing device in response to input received from the button interface panel. The apparatus can comprise a detec-tor. The detector can be configured to determine if an eye of a patient is open, the control system configured to operate the dispensing device in response to input received from the detector.

In various aspects, the main wearable headset comprises a bottom and a sidewall extending from the bottom. The bottom can have an exterior surface formed with a concave curvature and a recess, the bottom configured to be placed on the face of a patient such that the recess accommodates a nose of the patient. The apparatus can comprise a second dispensing device and a second aperture in the housing, wherein the first and second apertures are formed in the bottom of the wearable headset, the first and second aper-tures configured to be spaced at a distance such that when the wearable headset is positioned on a face of a patient at least a portion of each aperture is aligned with each eye of the patient. The apparatus can comprise a central mount and a bracket configured for assembly of the dispensing device and the control system.

In some aspects, the apparatus can comprise a central mount and a bracket configured for assembly of the dis-pensing device and the control system. The first and second dispensing devices can be mounted on opposite sides of the central mount, and the control system can be mounted to the bracket, each of the dispensing devices positioned such that the opening of each eye drop bottle is aligned with the first and second apertures, respectively, of the wearable headset. The central mount can be adjusted such that the opening of each eye drop bottle is approximately a pupil distance measured on the patient. The apparatus can comprise a heads up display and LEDs (light emitting diodes).

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the disclosure. Moreover, in the drawings, like reference numerals designate corresponding parts throughout the several views.

DETAILED DESCRIPTION

Figure 1:
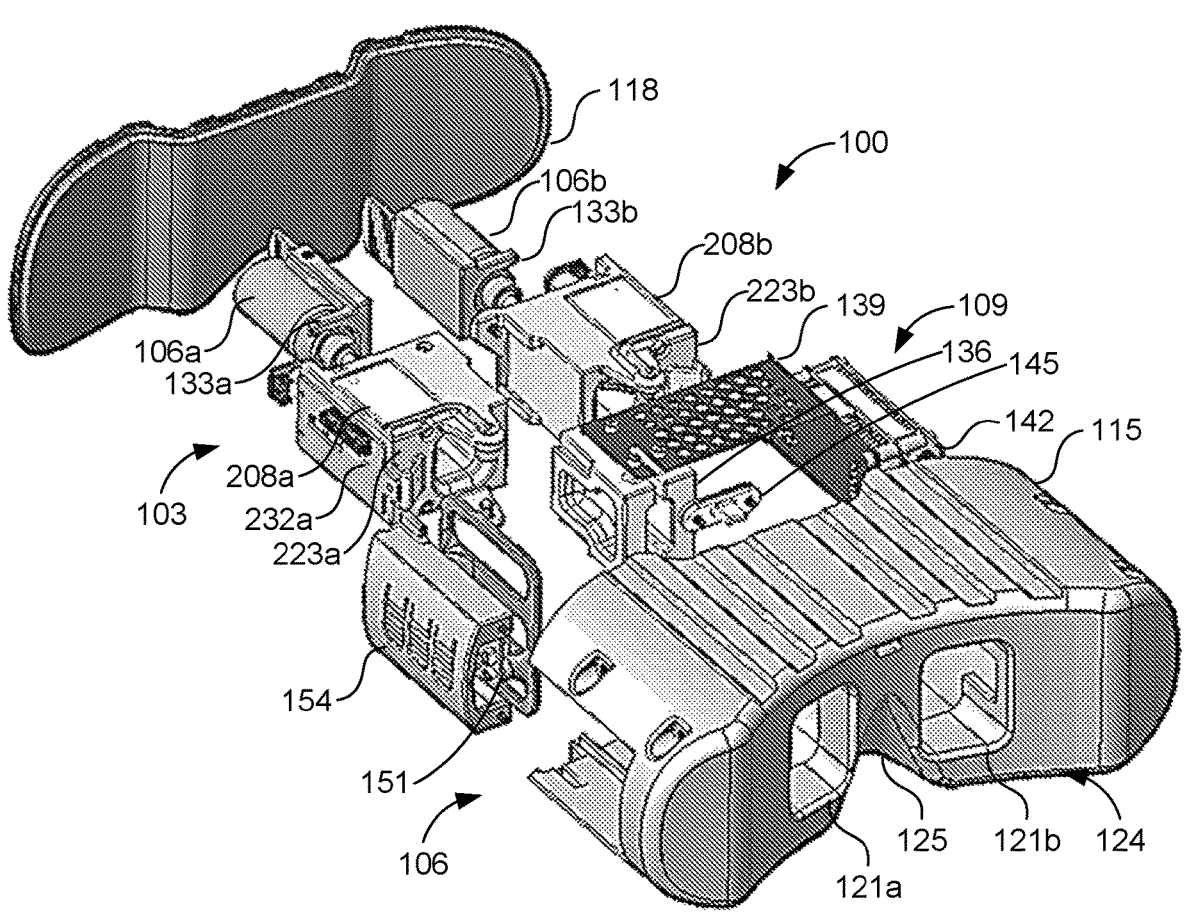
FIG. 1 illustrates an example of an exploded view of an apparatus for installation of eye drop, according to various embodiments of the present disclosure.

Described below are various embodiments of the present devices and methods for automated delivery of ophthalmological medications. Although this disclosure may refer to ophthalmological medications, fluid medications, or ophthalmological solutions, these term should be interpreted in the broadest form to include non-medicated and/or non-prescription fluid that may be instilled in the eye, such as lubricating or tear-replacing solutions. Although particular embodiments are described, those embodiments are mere exemplary implementations of the system and method. One skilled in the art will recognize other embodiments are possible. All such embodiments are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiment or embodiments disclosed herein. On the contrary, the intent is to cover all alternatives, modifications and equivalents included within the spirit and scope of the disclosure.

In accordance with a non-limiting example of the present disclosure, the apparatus for installation of eye drops, also called an automated eye dropper, provides means automated delivery of ophthalmological fluids to instill a predetermined dosage in one or both eyes of a patient, separately or simultaneously, in response to predetermined factors. The apparatus, also called an automated eye dropper, can be worn by the patient using an adjustable head strap, placed over the eyes of the patient when the patient is lying down, or be mounted in an adjustable manner on an arm or other extension to be positioned while the patient is sitting in a reclined position or lying down. A dosage can be administered without the tip of the bottle being in contact with the eye of the patient, thus minimizing contamination of the ophthalmological fluid. While the dosage of the fluid ophthalmological medication is predetermined and the dispensing is automatic, the delivery of the dosage to the eye or eyes of the patient is dependent on proper alignment of the respective bottle opening to the eye, in a substantially vertical position, and gravity for delivery of the dosage. While not recommended, it is possible to configure the apparatus to deliver the dosage to a patient that is not fully reclined. In that case, the rapid compression of the bottle would be necessary.

In a preferred embodiment, a dispensing device comprising a motor that rotates a lead screw can be used to dispense the fluid medication in a proper dosage. A movable mount can be threaded on the lead screw and prevented from rotation which causes the movable mount to move along the lead screw, translating in a direction same as the orientation of the axis of the bottle. The movable mount can be connected to the immovable plate through linkages. The linkages can include a yoke that attach at a point that allows free rotation and a pair of pivot arms that attach to the movable mount. As the lead screw rotates and the movable mount moves, the twin arm yoke assembly can push against the bottle increasing the pressure in the bottle. After the drop is instilled, the motor can be signaled to rotate in the other direction to the home location to get ready for the next instillation. The lead screw motor assembly and linkages provide an advantage of requiring less space to operate and the possibility of very rapid compression through changing the rpm of the motor. Each dispensing device can be controlled by a local board separate from the main controller. In an embodiment of the apparatus, there are two such dispensing devices, one for each eye. The drops can be dispensed sequentially, with sufficient time in between to allow the patient to blink a few times. Although possible, it is preferred that the drops not be instilled at simultaneously in both eyes because a dosage may be lost due to reflex blinking that may occur if one drop reaches an eye even slightly before the second in the other eye.

In an embodiment of the invention, the dispensing device is designed to detect the detachment of the drop so that the motor can stop rotating thereby prevent instillation of multiple drops. In an embodiment, a LED and a light sensor pair can be placed just below the exit of the bottle so that the drop creation blocks the light. In normal conditions, the sensor can detect the LED light. The sensor can detect the start of drop formation when the light is blocked, then senses breakup when the sensor starts to receives the light from the LED. By positioning the sensor very close to the exit from the bottle, the time at which drop detaches can be accurately determined, and immediately signal the motor to reverse the direction of rotation. If a satellite drop is formed at the tip after the drop breakup, the secondary drop can be sucked back into the bottle as the motor reverses direction of rotation. In another embodiment, the duration of the rotation of the motor can be fixed a priori to dispense just one drop. Since the deformation of the bottle that is required to create the drop increases as the remaining volume of the formulation in the bottle decreases, the duration of the rotation of the motor increases with each eye drop instillation and so the dispensing device can calculate and track of the number of drops instilled.

In another embodiment, a drop dispensing devices can be mounted in the apparatus housing to treat a single eye of a patient. In another embodiment, two drop dispensing devices (one for each eye) can be mounted in an apparatus housing with a variable space in between to adjust the spacing to meet the needs of the patient. In another embodiment, the entire housing can be rotated about a central fulcrum to adjust the orientation of the bottles for the drops to reach a preferred position in the eye.

Shown in FIGS. 1-4 is an example of apparatus for installation of eye drops or automated eye dropper 100. In an embodiment, the automated eye dropper 100 comprises: a dispensing device 103 configured to dispense a dosage of a fluid medication from an eye drop bottle 106. A control system 109 can be operatively connected to the dispensing device 103. A housing 112 comprising a main wearable headset 115 and a cover 118 can be configured to contain the dispensing device 103 and the control system 109. The housing 112 is also configured to allow passage of the dosage of the fluid medication (eye drops) through an aperture 121 in the main wearable headset 115 of the housing 112. In an embodiment, the automated eye dropper 100 can comprise a button interface panel 154 operatively connected to the control system 109. The control system 109 configured to operate the dispensing device 103 in response to input received from the button interface panel 214. In an embodiment, the automated eye dropper can further comprise a camera 245 configured to determine if an eye of a patient is open. The control system 109 can be configured to operate the dispensing device 103 in response to input received from the camera 245. The control system 109 can comprise one more controllers comprising a printed circuit board (PCB). For example the controller may be at least one of: a main controller, a controller for the motor, a controller for a camera including storage, a controller to connect the dispensing device to a network, a controller to limit the motor, a controller for providing visual or audio cues to the patient, and the like.

Shown in FIG. 1 is an exploded view of the automated eye dropper 100, shown in a non-limiting example with two dispensing devices 103. The automated eye dropper 100 comprising: a housing 115 configured to contain a pair of dispensing devices 103a, 103b and a control system 109. Each dispensing device 103a, 103b comprises a lead screw motor assembly 130, removable bottle magazine 133, and drop bottles 106. In some embodiments, the removable bottle magazine 133 can be configured to receive a standard size eye drop bottles 106. Each eye drop bottle 106 can have a removable cap 107, such that the eye drop bottle 106 can be sealed to prevent contamination when not in use and the cap 107 removed prior to use of the automated eye dropper 100 on a patient.

A central mount 136 comprises a bracket 139 to hold a main controller 142 of the control system 109. Each of the dispensing devices 103a, 103b are also mounted to the central mount 136. The central mount 136 can be configured to mount one or two dispensing devices 103a, 103b. In some embodiments, the automated eye dropper 100 further comprises a heads up display 145 and LEDs (light emitting diodes) 148, which can also be attached to the central mount 136. A button controller 151 can be operatively connected to the main controller 142 and a button interface panel 154 which can be attached to the main wearable headset 115 to control the automated eye dropper 100. In an embodiment, the central mount 136 can be configured for the first and second dispensing devices 103a, 103b to be mounted on opposite sides of the central mount 136, and the control system 109 mounted to the bracket 139, each of the dispensing devices 103a, 103b positioned such that the opening of each eye drop bottle 106a, 106b is aligned with the first and second apertures 121a, 121b, respectively, of the wearable headset 115. In some embodiments, the central mount 136 can be adjusted such that the opening of each eye drop bottle 106a, 106b is approximately a pupil distance measured on the patient (not shown). The main wearable headset 115 can have a bottom 124 and a sidewall 127 extending from the bottom 124. The bottom 124 can have an exterior surface formed with a concave curvature and a recess 125. The bottom 124 configured to be placed on the face of a patient such that the recess 125 accommodates a nose of the patient.

Figure 2:
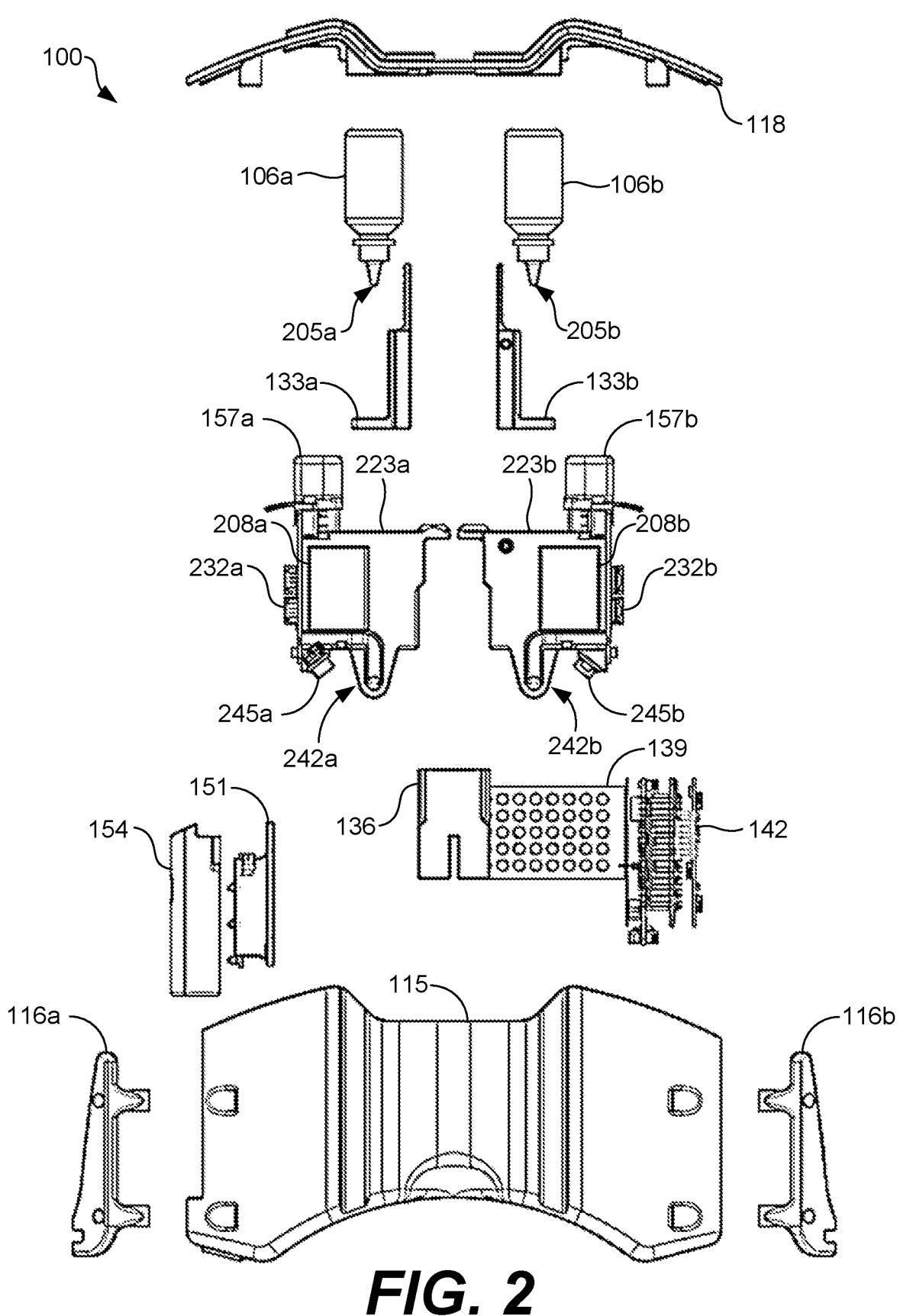
FIG. 2 illustrates an example of a top exploded view of the apparatus for installation of eye drops of FIG. 1, according to various embodiments of the present disclosure.

Turning for FIG. 2, a top exploded view further illustrates the details of the automated eye dropper 100. In an embodiment, head strap mounts 116 can also be attached to the main wearable headset 115 to accommodate a head strap (not shown) when in use or worn by a patient.

Figure 3:
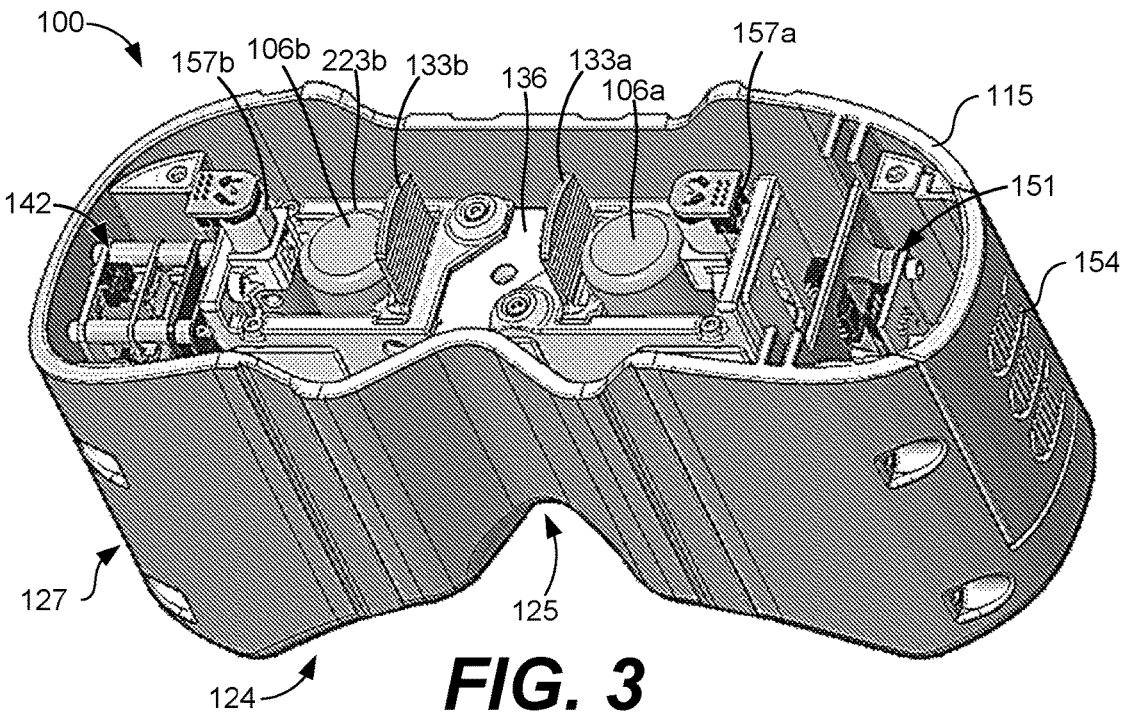
FIG. 3 illustrates an example of an assembled view of the apparatus for installation of eye drops of FIG. 1, shown with the cover removed, according to various embodiments of the present disclosure.

Shown in FIG. 3 is an embodiment of the automated eye dropper 100 assembled with the cover 118 removed. As shown, two dispensing devices 103*a*, 103*b* are mounted on the central mount 136 in opposing directions. As shown, the housing 112, in particular the wearable headset 115, contains the dispensing device 103 and the control system 109.

Figure 4:
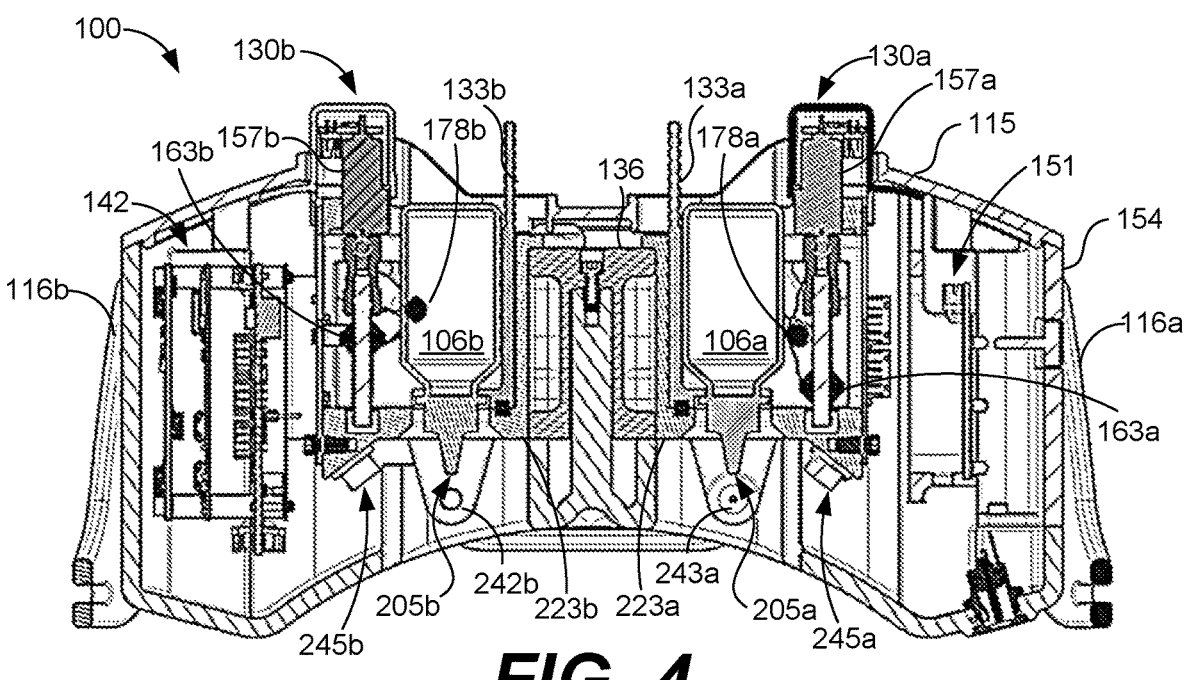
FIG. 4 illustrates an example of a cross-sectional view of the assembled apparatus for installation of eye drops of FIG. 1, according to various embodiments of the present disclosure.

A cross-sectional view of the assembled automated eye dropper 100 is shown in FIG. 4. In this view, the lead screw motor assembly 130*b*, shown on the left, illustrates the movable mount 163*b* in a raised position on the lead screw 160 such that the shaft 178*b* of the yoke 175*b* engaged with the bottle 106*b* to dispense eye drops. Shown on the right, the movable mount 163*a* in a lowered position on the lead screw 160 and the shaft 178*a* of the yoke 175*a* disengaged from the bottle 106*a*. In an embodiment, the central mount 136 can be replaced with an alternate central mount to provide a wider or narrower distance between the bottles 106*a*, 106*b* depending on the pupil distance of the patient. In an embodiment, the central mount 136 can be adjusted within the housing to provide a wider or narrower distance between the bottles 106*a*, 106*b* depending on the pupil distance of the patient.

Figure 5:
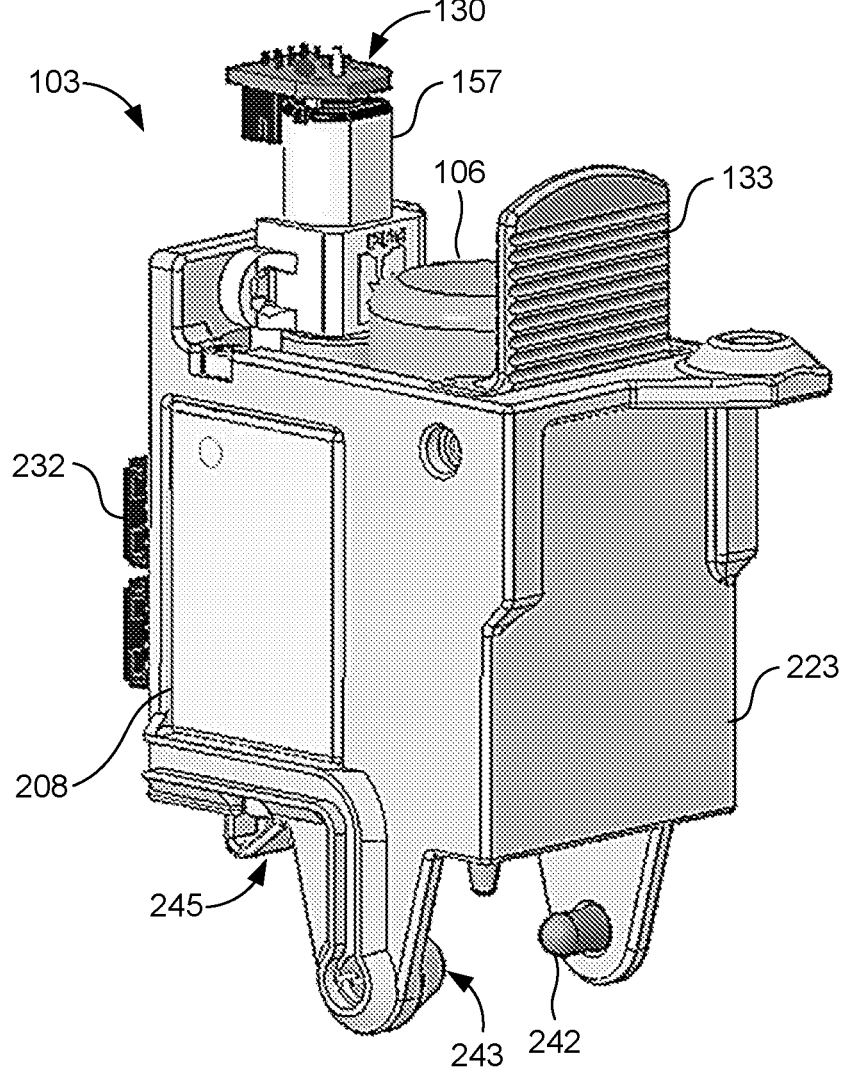
FIG. 5 illustrates an example of an isometric view of a dispensing device, according to various embodiments of the present disclosure.

Turning to FIG. 5 an isometric view of a dispensing device 103 configured to contain the lead screw motor assembly 130 and a removable bottle magazine 133 with eye drop bottle 106. In an embodiment, the dispensing device 103 can be provided as a cartridge to be used in an apparatus 100 to instill eye drops in one or both eyes of a patient. In an embodiment, the dispensing device 103 can be provided as a cartridge to be used in an apparatus or system configured to seat the dispensing device 103.

Figure 6:
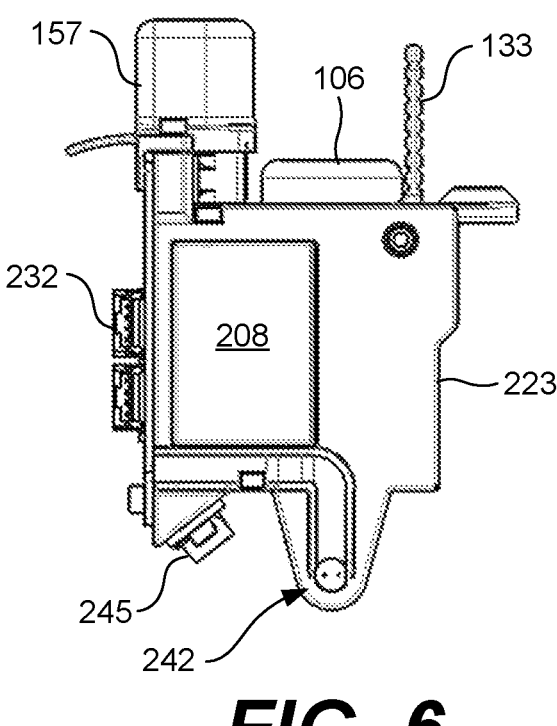
FIG. 6 illustrates an example of a side view of the dispensing device of FIG. 5, according to various embodiments of the present disclosure.
Figure 7:
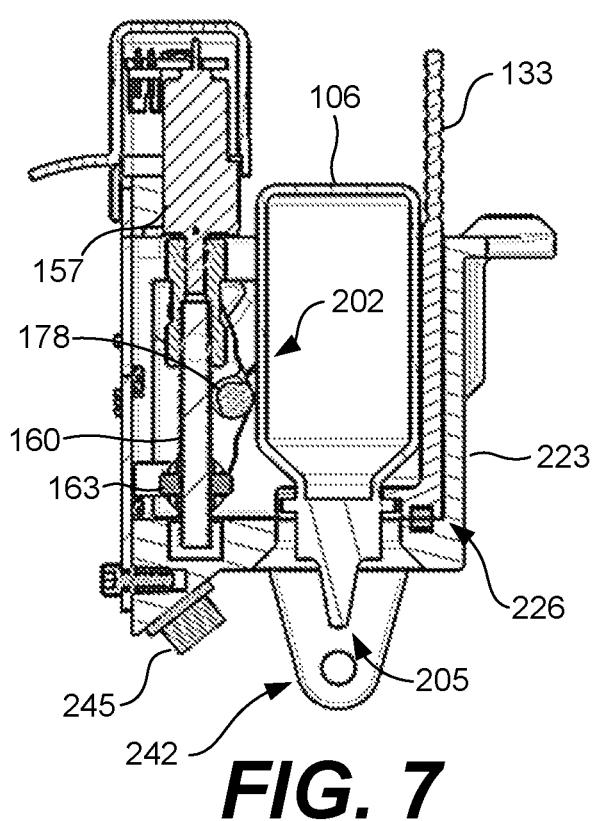
FIG. 7 illustrates an example of a cross-sectional view of the dispensing device of FIG. 5, according to various embodiments of the present disclosure.

Next in FIGS. 6 and 7, greater detail of dispensing device 103 is shown in a side view and cross-sectional view, respectively. In an embodiment, the dispensing device 103 contains lead screw motor assembly 130 which can be operated to engage with a deformable side 202 of an eye drop bottle 106. As shown in FIG. 7, the lead screw motor assembly 130 is in an off position with the movable mount 136 lowered and the shaft 178 of the yoke 175 disengaged from the side 202 of the bottle 106. When the lead screw motor assembly 130 is activated, the movable mount moves upwards, such that the shaft 178 of the yoke 175 moves upward and to the side, along the curved path, putting the shaft 178 in contact with the eye drop bottle 106 resulting in pressure on the side 202 of the bottle 106. In an embodiment, the yoke 175 can be configured to move a fixed distance. In an embodiment, the yoke 175 can be configured to move along the curved path applying more pressure until the LED 242 with sensor 243 detects that a drop has been released.

Figure 8:
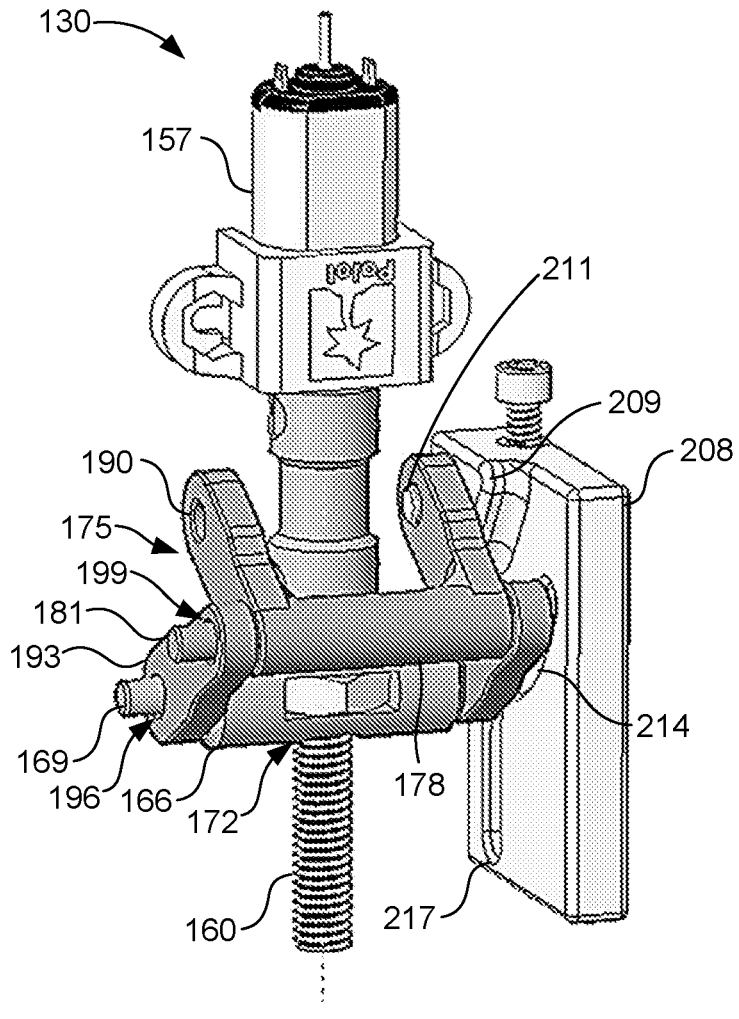
FIG. 8 illustrates an example of an isometric view of a lead screw motor assembly, according to various embodiments of the present disclosure.

FIG. 8 show the lead screw motor assembly 130 in greater detail. The motor 157 can be connected to a lead screw 160. The motor 157 can be configured to rotate the lead screw 160 in either a first rotational direction or a second rotational direction. For example, the first rotational direction can be clockwise and the second rotational direction can be counter clockwise. In another example, the first rotational direction can be counter clockwise and the second rotational direction can be clockwise. A movable mount 163 comprising a mount body 166, a pair of opposing mount pins 169, and a threaded hole 172 that transverses the mount body 166 in a direction orthogonal to the opposing mount pins 169. The movable mount 163 can be threaded on the lead screw 160 via the threaded hole 172. The moveable mount 163 configured to translate on the lead screw 160 in a first direction, when the lead screw 160 is rotating in a first rotational direction, and a second direction, when the lead screw 160 is rotating in a second direction. A yoke 175 comprising a shaft 178 with a pair of opposing yoke pins 181 and a pair of yoke arms 184 extending orthogonally from the shaft 178, each yoke arm 184 having a distal end with a yoke hole 190. The yoke 175 configured to pivot about a fixed position via the pair of yoke holes 190. A pair of pivot arms 193, each pivot arm 193 having a mount aperture 196 and a pivot aperture 199, each mount aperture 196 configured to receive the respective mount pin 169. Each pivot aperture 199 configured to receive the respective yoke pin 181, each pivot arm 193 pivotably connected to the mount 163 and the yoke 175. A bottle 106 containing a fluid having a deformable side 202 and having an opening 205, the bottle 106 positioned at a distance from the shaft 178 of the yoke 175 such that in response to movement of the movable mount 163, the shaft 178 of the yoke 175 is configured to move in a curved path and press the deformable side 202 of the bottle 106 to dispense the fluid.

The dispensing device 103 further comprising a pair of slotted plates 208. Each slotted plate 208 having a relief 209 with a pin 211 configured to receive the yoke 175 via the respective yoke holes 190. Each slotted plate 208 having a curved slot 214 configured to receive and guide the respective yoke pin 181. Each slotted plate 208 having a linear slot 217 configured to receive and guide the respective mount pin 169. In some embodiments, the curved slot 214 is connected to the linear slot 217.

The dispensing device 103, further comprising a removable bottle magazine 133 configured to receive the bottle 106 containing the fluid. The dispensing device 103 further comprising a dispenser housing 223 comprising a seat 226 and a dispensing aperture 229. The seat 226 configured to receive the bottle magazine 133. In some embodiments, the slotted plate 208 is fixed to the dispenser housing 223. In some embodiments, the slotted plate 208 is integrally formed in the dispenser housing 223.

The dispensing device 103, further comprises a local control processor 232 configured to control the motor 157. The dispensing device 103 further comprising a lower limit switch 235 configured to send a signal to turn off the motor 157, in response to the movable mount 163 triggering the lower limit switch 235. The dispensing device 103, further comprising an upper limit switch 238 configured to send a signal reverse the rotational direction of the motor 157, in response to the movable mount 163 triggering the upper limit switch 238. The dispensing device 103, further comprising a drop sensing LED 242 and light sensor 243 configured to send a signal reverse the rotational direction of the motor, in response to the drop light sensor 243 detecting that the dosage has been released. In an embodiment, the dispensing device 103 comprises a camera 245.

Figure 9:
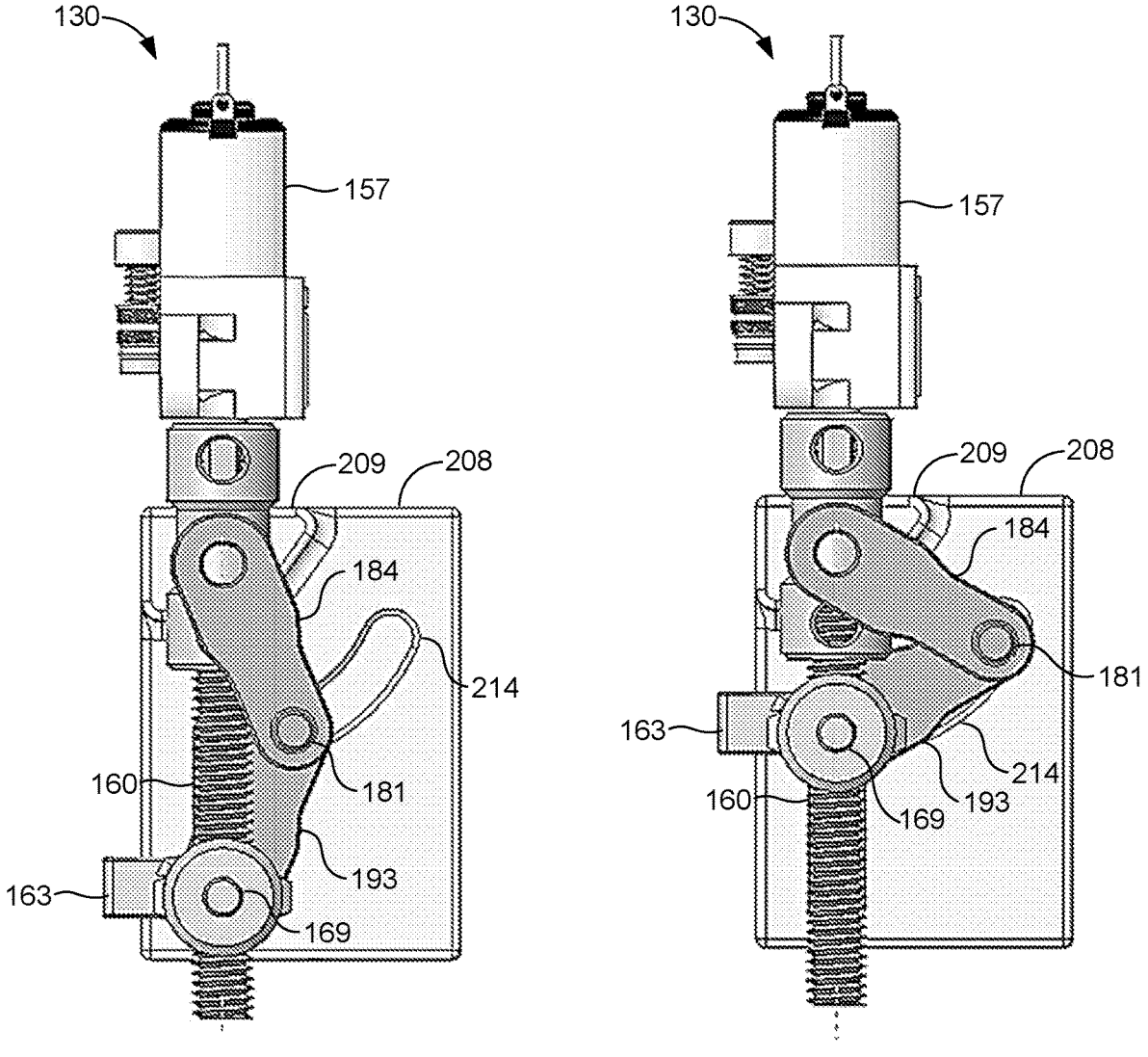
FIGS. 9A and 9B illustrate an example of a side view of a lead screw motor assembly of FIG. 8, with the front pivot arm removed, in an off position (FIG. 9A) and an engaged position (FIG. 9B), according to various embodiments of the present disclosure.

The operation of the lead screw motor assembly 130 is illustrated in FIGS. 9A and 9B. In an embodiment, the dispensing device 103 can be powered on upon a press of a button and a programming sequence is initiated. The motor 157 turns the lead screw 160, for example clockwise, moving the movable mount 163 upwards along the lead screw 160, decreasing the distance between the movable mount 163 and the motor 157. There can be three linkages: one yoke 175 and two pivot arms 193. The yoke 175 can be pinned to front and rear plates 208 in a fixed location at by distal end of each yoke arm 184 via each yoke hole 190 and the yoke 175 is free to pivot about the pin 211. The pivot arms 193 are pinned to the movable mount 163 on one end via mount aperture 196 and the free-moving end of the yoke 175 via the pivot aperture 199. As the movable mount 163 moves upwards, the shaft 178 of the yoke 175 can be forced to move upward and to the side, along the curved path. When the yoke 175 is in contact with the eye drop bottle 106, the shaft 178 exerts pressure on the bottle 106 until the drop is released. The drop-sensing IR LEDs 242 detect when a drop is released and sends the motor 157 of the lead screw motor assembly 130 into the retract operation. In the event that there is not a bottle 106 loaded in the dispensing device 103, the movable mount 163 will trigger an upper limit switch 238, which prevents the control system 109 from crashing. The upper limit switch 238 trigger sends the lead screw motor assembly 130 into retraction mode.

For the retraction operation, the motor 157 turns the lead screw 160 in an opposite direction, for example counter clockwise, moving the movable mount 163 downwards along the lead screw 160, increasing the distance between the mount 163 and the motor 157. The yoke 175 and the pivot arms 193 rotate downward and straighten out, moving the yoke 175 out of contact and away from the eye drop bottle 106. When the moveable mount 163 triggers a lower limit switch, a signal can be sent to the motor 157 to stop turning.

Figure 10:
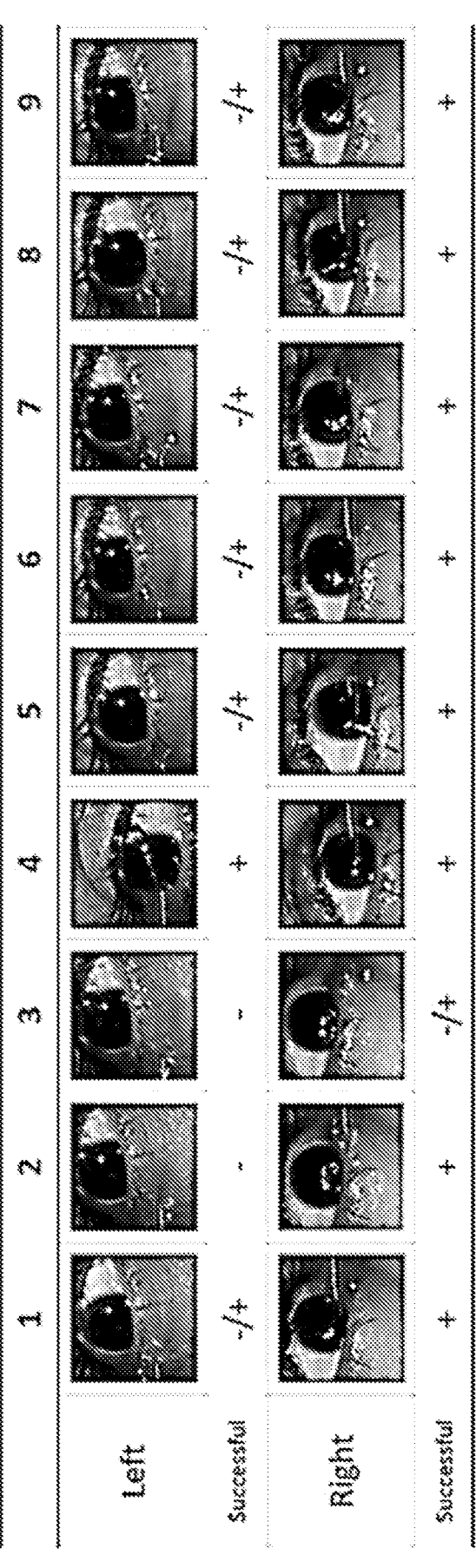
FIG. 10 illustrates experimental results of the moment a drop reaches the eye (both left and right) in a series of nine tests, according to various embodiments of the present disclosure.

Turning next to FIG. 10, experimental results from testing of the automated eye dropper 100 are shown. For each test, the automated eye dropper 100 was placed on the eyes of a patient, the patient was asked to continuously blink until an LED turned green (indicating that a drop would coming out soon), and then stop blinking. Typically, there is a reflex blink in both eyes as soon as a drop hits either eye. If dropped at the same time, there can be slight differences in the time needed for each of the two drops to hit respective eyes, so the drop that hits later will likely hit the closing eyelid and not reach the eye. For this experiment, drops were instilled in both eyes, one after the other. This test was conducted nine times on the same patient and was effective in that the eye blink did not lead to drops hitting the eyelid. Each test generated a video for each eye, obtained from internal cameras 245 in the automated eye dropper 100. The videos were analyzed to find frames in which the fluid coming out was hitting the eyes. The time stamps are not same for left and right, because the drops were instilled one after the other. The selected frames are shown for the left and right eye in each of the nine tests, with the drop moving so fast that in any frame (about 1/30 second) it travels a fair distance so it looks like a jet. In each frame of the series, the moving drop appears to be a jet of fluid hitting the eye, eyelid, or just below the eyelid. From the selected frames the effectiveness of a drop landing on the eye was determined to be: successful (+), partially successful (−/+), or unsuccessful (−). In this example series of tests, it was determined that the right eye had more successful instillation compared to left because of the way the automated eye dropper 100 was positioned or sitting on the face of the patient. Thus, proper placement and orientation of the device on the face of the patient can affect the instillation process. In an embodiment, an optional LED (not shown) can be attached to the tip of the eye dropper to facilitate the alignment of the eye of the patient with the tip 205 of the bottle 106, such that by just by looking at the optional LED the patient can center the eye drop bottle 106 on the eye. For example, the device could be moved until the reflection is in line with the optional LED, which would indicate alignment.

Figure 11:
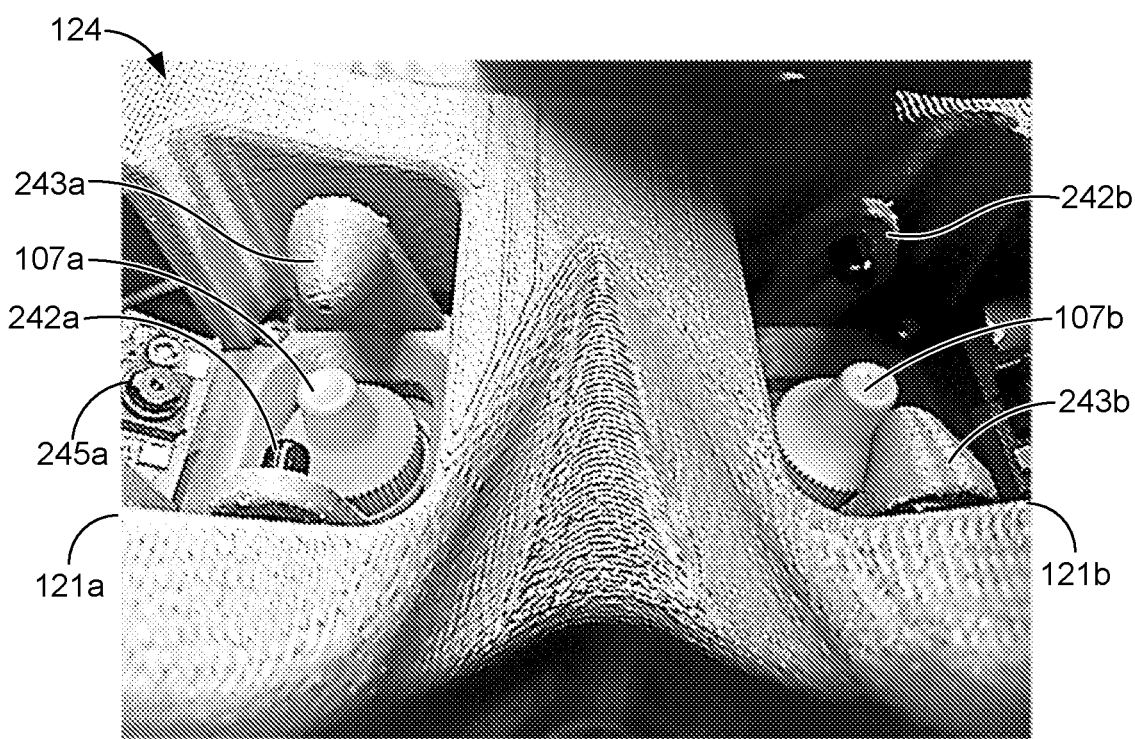
FIG. 11 illustrates the placement of the eye dropper bottles within the automated eye dropper as viewed through the bottom, according to various embodiments of the present disclosure.
Figure 12:
FIG. 12 illustrates accessibility of the caps of each bottle through the apertures without removing the bottles from the automated eye dropper, according to various embodiments of the present disclosure.

FIG. 11 illustrates the placement of the eye dropper bottles 106 within the automated eye dropper 100, as viewed from the bottom 124. As shown, the cap 107 seals each of the bottles 106 when not in use. Each cap 107 is accessible through the respective aperture 121 and must be removed to expose the tip 205 of the bottle 106 before using the automated eye dropper 100. FIG. 12 shows that the cap 107 of the bottle 106 can be removed without removing the bottles 106 from the device 100. However, some patients may find the cap 107 difficult to reach and remove due to the position of the bottle 106 between the LED 242 and sensor 243, and recessed location within the automated eye dropper 100. In some embodiments, the cap 107 may be adapted to receive an optional attachment 251 to facilitate the removal and replacement of the cap 107 on the bottle 106. In some embodiments, the cap 107 may be removed by a tool to facilitate the removal and replacement of the cap 107 on the bottle 106.

Figure 13:
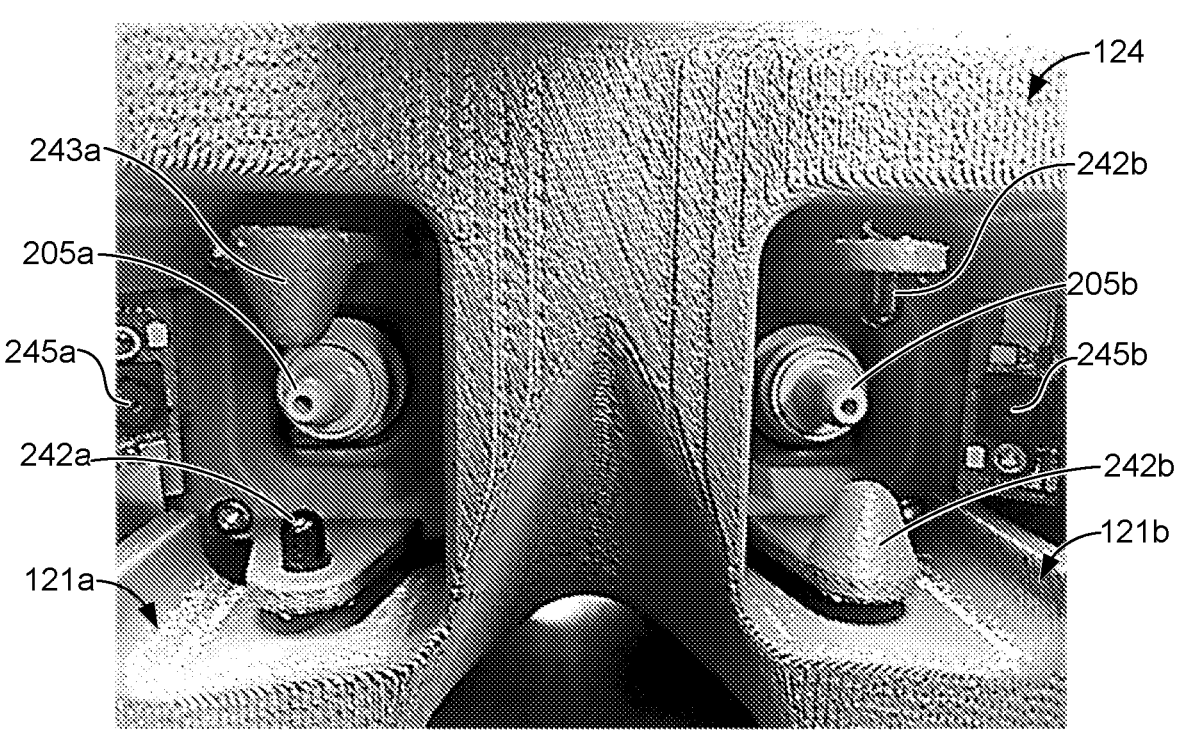
FIG. 13 illustrates the automated eye dropper with the caps removed and ready for use with the patient (not shown), according to various embodiments of the present disclosure.
Figure 14:
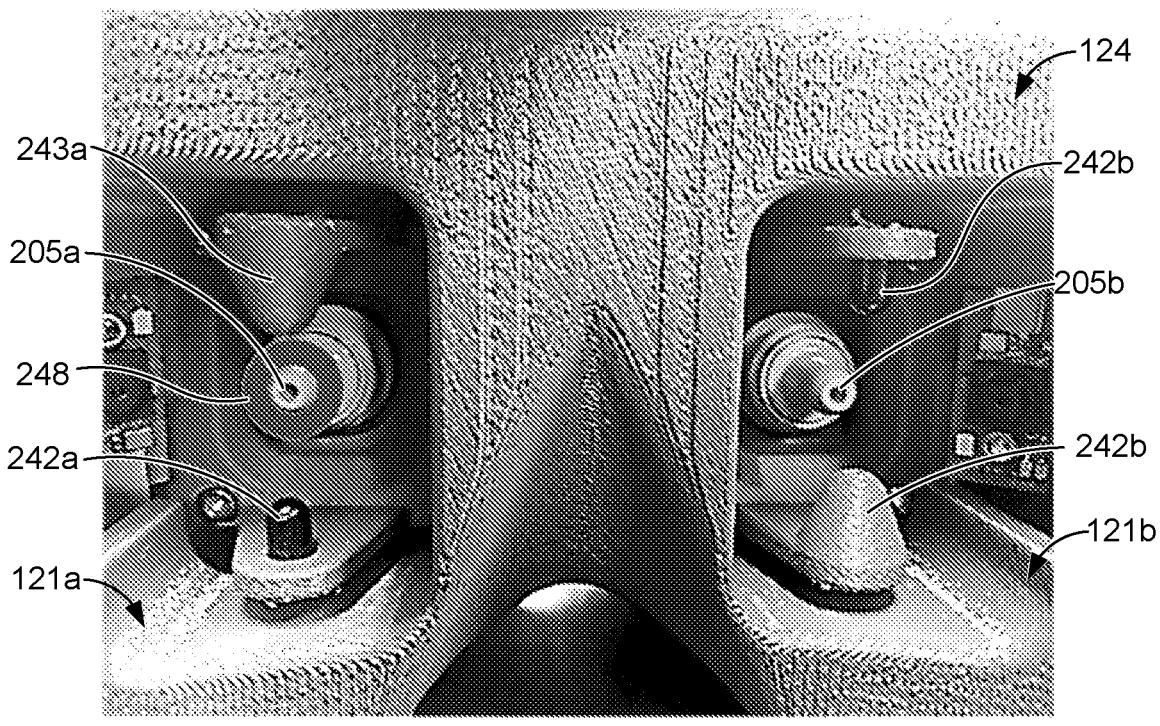
FIG. 14 illustrates an optional target on one of the bottles and an approximate zone for the patient to focus for instillation of the drops, according to various embodiments of the present disclosure.

FIG. 13 depicts the device 100 with the caps 107 removed and ready for use with the patient (not shown). The tip 205 of each bottle 106 on each side is shown between the LED 242 and sensor 243 which detects that a drop has been released. Each camera 245 is also shown, with the location and orientation of the camera 245 critical to obtain a good video. FIG. 14 illustrates an approximate zone for the patient to focus on the tip 205 of a bottle 106 for successful instillation of the drops. In some embodiments, a washer or target 248 may optionally be applied to the top of the bottle 106 near the tip 205, to provide a visual target for orientation of the eye of the patient. By looking at the tip 205 and/or washer 248, the patient can visually center the automated eye dropper 100 on the eye.

Figure 15:
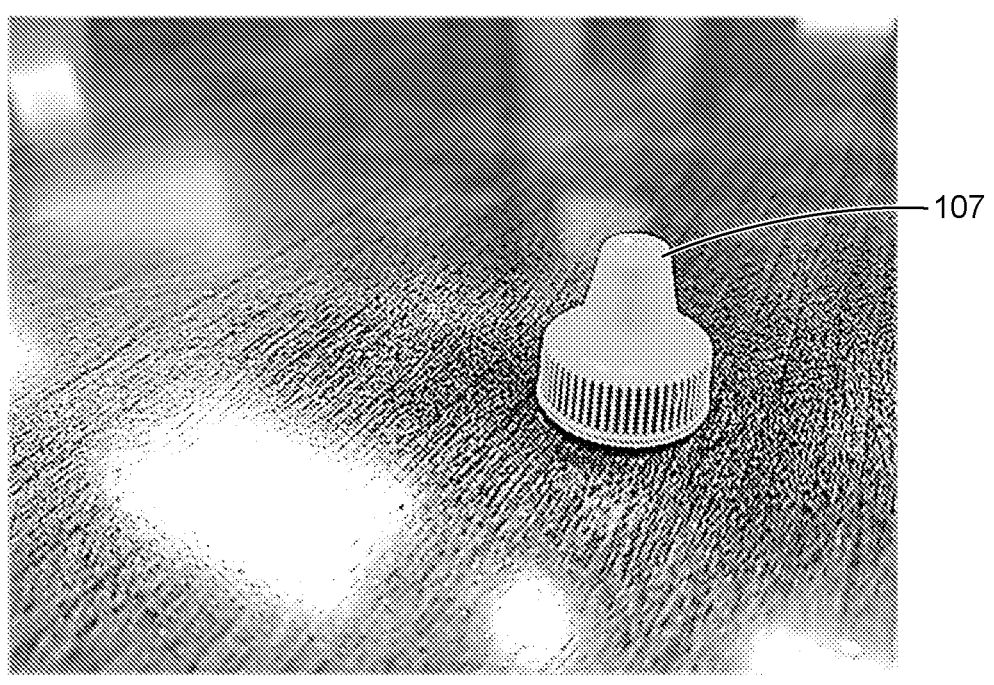
FIG. 15 illustrates a cap of the bottle removed, according to various embodiments of the present disclosure.
Figure 16:
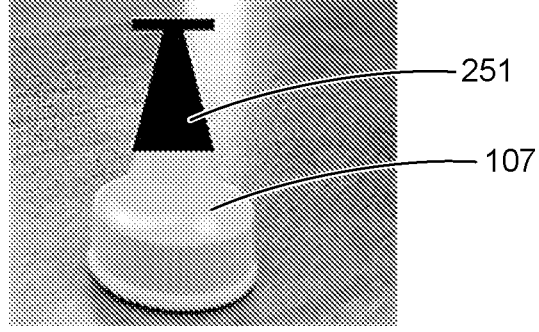
FIG. 16 illustrates the design of a piece that can be attached to the bottle cap to facilitate easy removal (before instilling the drops) and replacement (after instillation of the drops) of the cap, according to various embodiments of the present disclosure.

Next, FIG. 15 shows an example of a cap 107 removed from the bottle 106. As shown in FIG. 12, it can be difficult for some patients to reach and twist the cap 107 to remove it from the bottle 106 prior to use. For example, a patient with large hands or a geriatric patient may not have the dexterity to grip the cap 106 in a recessed and confined space through the aperture 121. FIG. 16 illustrates an example of an attachment 251 that can optionally be applied to each cap 107 to assist with the removal and replacement of the cap 106. The attachment 251 can be sized based on the dimensions of a cap 107 (FIG. 15) and adapted to have a larger diameter top that can extend beyond the LED 242 and sensor 243 when the cap 107 is secured on the bottle 106. In some examples, the attachment 251 can be ergonomic to allow for a better grip.

It is emphasized that the above-described embodiments of the present disclosure are merely possible examples of implementations set forth for a clear understanding of the principles of the disclosure. Many variations and modifications may be made to the above-described embodiments without departing substantially from the spirit and principles of the disclosure. All such modifications and variations are intended to be included herein within the scope of this disclosure and protected by the following claims.

The invention claimed is:

1. An apparatus for installation of eye drops, the apparatus comprising:
a dispensing device configured to dispense a dosage of a fluid from an eye drop bottle, the dispensing device comprising:

a motor connected to a lead screw, the motor configured to rotate the lead screw in either a first rotational direction or a second rotational direction;

a movable mount comprising a body, a pair of opposing mount pins, and a threaded hole that transverses the body in a direction orthogonal to the opposing mount pins, wherein the movable mount is threaded on the lead screw via the threaded hole, the moveable mount configured to translate on the lead screw in a first direction, when the lead screw is rotating in the first rotational direction, and a second direction, when the lead screw is rotating in the second rotational direction;

a yoke comprising a shaft with a pair of opposing yoke pins and a pair of yoke arms extending orthogonally from the shaft, each yoke arm having a distal end with a yoke hole, the yoke configured to pivot about a fixed position via the pair of yoke holes;

a pair of pivot arms, each pivot arm having a mount aperture and a pivot aperture, each mount aperture configured to receive the respective mount pin, each pivot aperture configured to receive the respective yoke pin, each pivot arm pivotably connected to the mount and the yoke; and the eye drop bottle containing the fluid, the eye drop bottle having a deformable side and having an opening, the eye drop bottle positioned at a distance from the shaft of the yoke such that in response to movement of the movable mount, the shaft of the yoke is configured to move in a curved path and press the deformable side of the eye drop bottle to dispense the fluid;

a control system operatively connected to the dispensing device; and a housing, the housing comprising a main wearable headset and a cover, the housing configured to contain the dispensing device and the control system, and the housing configured to allow passage of the dosage of the fluid through an aperture in the main wearable headset of the housing.

2. The dispensing device of claim 1, further comprising a pair of slotted plates, each slotted plate having a relief with a pin configured to receive the yoke via the respective yoke holes, each slotted plate having a curved slot configured to receive and guide the respective yoke pin, each slotted plate having a linear slot configured to receive and guide the respective mount pin.

3. The dispensing device of claim 2, wherein the curved slot is connected to the linear slot.

4. The dispensing device of claim 1, further comprising:

a removable bottle magazine configured to receive the eye drop bottle containing the fluid; and a dispenser housing comprising a seat and a dispensing aperture, the seat configured to receive the bottle magazine.

5. The dispensing device of claim 4, wherein a slotted plate is fixed to the dispenser housing.

6. The dispensing device of claim 4, wherein a slotted plate is integrally formed in the dispenser housing.

7. The dispensing device of claim 1, further comprising a local control processor, the local control processor configured to control the motor.

8. The dispensing device of claim 7, further comprising a lower limit switch, the lower limit switch configured to send a signal to turn off the motor, in response to the movable mount triggering the lower limit switch.

9. The dispensing device of claim 1, further comprising an upper limit switch, the upper limit switch configured to send a signal to reverse the rotational direction of the motor, in response to the movable mount triggering the upper limit switch.

10. The dispensing device of claim 1, further comprising a drop sensing LED configured to send a signal to reverse the rotational direction of the motor, in response to the drop sensing LED detecting that the dosage has been released.

11. An apparatus for installation of eye drops, the apparatus comprising:

first and second dispensing devices, each of the first and second dispensing devices configured to dispense a dosage of a fluid medication from an eye drop bottle, each of the first and second dispensing devices comprising:

a motor connected to a lead screw, the motor configured to rotate the lead screw in either a first rotational direction or a second rotational direction;

a movable mount comprising a body, a pair of opposing mount pins, and a threaded hole that transverses the body in a direction orthogonal to the opposing mount pins, wherein the movable mount is threaded on the lead screw via the threaded hole, the moveable mount configured to translate on the lead screw in a first direction, when the lead screw is rotating in the first rotational direction, and a second direction, when the lead screw is rotating in the second rotational direction;

a yoke comprising a shaft with a pair of opposing yoke pins and a pair of yoke arms extending orthogonally from the shaft, each yoke arm having a distal end with a yoke hole, the yoke configured to pivot about a fixed position via the pair of yoke holes;

a pair of pivot arms, each pivot arm having a mount aperture and a pivot aperture, each mount aperture configured to receive the respective mount pin, each pivot aperture configured to receive the respective yoke pin, each pivot arm pivotably connected to the mount and the yoke; and the eye drop bottle containing the fluid medication, the eye drop bottle having a deformable side and having an opening, the eye drop bottle positioned at a distance from the shaft of the yoke such that in response to movement of the movable mount, the shaft of the yoke is configured to move in a curved path and press the deformable side of the eye drop bottle to dispense the fluid medication;

a control system operatively connected to the first and second dispensing devices; and a housing, the housing comprising a main wearable headset and a cover, the housing configured to contain the first and second dispensing devices and the control system, and the housing configured to allow passage of the dosage of the fluid medication from the first or second dispensing device through a corresponding first or second aperture in the main wearable headset of the housing.

12. The apparatus for installation of eye drops of claim 11, further comprising a button interface panel operatively connected to the control system, the control system configured to operate the first and second dispensing devices in response to input received from the button interface panel.

13. The apparatus for installation of eye drops of claim 11, further comprising a detector, the detector configured to determine if an eye of a patient is open, the control system configured to operate the first or second dispensing device in response to input received from the detector.

14. The apparatus for installation of eye drops of claim 11, wherein the main wearable headset comprises a bottom and a sidewall extending from the bottom.

15. The apparatus for installation of eye drops of claim 14, wherein the first and second apertures are formed in the bottom of the main wearable headset, the first and second apertures configured to be spaced at a distance such that when the main wearable headset is positioned on a face of a patient at least a portion of each aperture is aligned with each eye of the patient.

16. The apparatus for installation of eye drops of claim 14, wherein the bottom has an exterior surface formed with a concave curvature and a recess, the bottom configured to be placed on a face of a patient such that the recess accommodates a nose of the patient.

17. The apparatus for installation of eye drops of claim 11, further comprising a central mount and a bracket configured for assembly of the first and second dispensing devices and the control system.

18. The apparatus for installation of eye drops of claim 17, wherein the first and second dispensing devices are mounted on opposite sides of the central mount, and the control system is mounted to the bracket, each of the first and second dispensing devices positioned such that the opening of each eye drop bottle is aligned with one of the first and second apertures, respectively, of the main wearable headset.

19. The apparatus for installation of eye drops of claim 18, wherein the central mount is configured to adjust position of the opening of each eye drop bottle to approximately align with a pupil on the patient.

20. The apparatus for installation of eye drops of claim 11, further comprising a heads up display and LEDs (light emitting diodes).

*  *  *  *  *